United States Patent [19]
Lane et al.

[11] Patent Number: 5,504,331
[45] Date of Patent: Apr. 2, 1996

[54] SPECTROSCOPIC ANALYZER OPERATING METHOD

[75] Inventors: Linda M. Lane, Long Beach; Timothy M. Davidson, Alta Loma, both of Calif.

[73] Assignee: Atlantic Richfield Company, Los Angeles, Calif.

[21] Appl. No.: 137,323

[22] Filed: Oct. 15, 1993

[51] Int. Cl.$^6$ ................................................. G01N 21/35
[52] U.S. Cl. .................. 250/339.09; 250/339.04; 250/339.07; 250/339.12; 250/343
[58] Field of Search .................. 250/339.09, 339.13, 250/252.1 A, 343, 339.04, 341.2, 339.07, 339.12

[56] References Cited

U.S. PATENT DOCUMENTS

| | | | |
|---|---|---|---|
| 4,549,080 | 10/1985 | Baskins et al. | 250/343 |
| 4,598,201 | 7/1986 | Fertig et al. | 250/343 |
| 4,963,745 | 10/1990 | Maggard | 250/343 |
| 5,068,798 | 11/1991 | Heath et al. | 250/343 |
| 5,082,985 | 1/1992 | Crouzet et al. | 250/339.12 |
| 5,124,553 | 6/1992 | Hilliard et al. | 250/344 |
| 5,349,188 | 9/1994 | Maggard | 250/339.12 |

*Primary Examiner*—Carolyn E. Fields
*Attorney, Agent, or Firm*—Joseph D. Yao

[57] ABSTRACT

Fluid samples, including petroleum fuels, may be analyzed as to certain properties such as octane number by a near infrared spectrometer by a method which carries out steps of verifying operating conditions of the spectrometer, comparing measured values of absorbance of radiation at predetermined wavelengths with a set of training values for the fluid composition in question and indicating an out of range condition when a predetermined set of measured values, when averaged, exceeds a predetermined limit. The system carries out a verification of its operating conditions by performing a routine analysis on a reference fluid, such as toluene. A so-called diagnostics routine may be performed to verify operating parameters of the system such as the radiation source, and the throughput of certain optical elements whose transmissivity may be affected by residue from the fluids being analyzed. Fluid specimens may be collected in a sample capture system having a plurality of sample capture vessels selectively operated to capture out of specification fluid samples.

15 Claims, 6 Drawing Sheets

SPECTROSCOPIC ANALYZER OPERATING METHOD

BACKGROUND OF THE INVENTION

1. Field of the Invention

The present invention pertains to a method of operating a near infrared spectroscopic analyzer particularly adapted for analyzing hydrocarbon fluid compositions.

2. Background

Near infrared spectroscopic analyzers are used in many petroleum refinery process applications for measuring several properties of refinery process fluids including crude oils, gasolines and other products. The basic methodology involving the use of near infrared (NIR) spectroscopic analyzers includes obtaining the near infrared spectra of a training set of sample fluids for which the properties of interest have been measured by traditional techniques. For example, in the case of using an NIR analyzer to measure octane numbers of motor gasoline, a set of gasoline samples would be measured by octane engines to obtain the requisite octane numbers. Models that relate the measured properties of the samples to their spectra may be generated using a computer and regression analysis software. These models would then allow the prediction of the properties of the unknown samples directly from their spectra measured by the spectrometer.

The model predictions are accurate as long as the unknown samples are sufficiently similar to the training set samples. Accordingly, when an "outlier" sample is detected, it can be for many reasons such as, the sample composition lies outside the training set composition range, the process stream has fundamentally changed due to an engineering design change, the near infrared analyzer instrument has undergone some mechanical or electrical change or the primary reference measurement is inaccurate, for example. With this many conditions which could result in a measurement of an outlier, it has been deemed desirable to develop a method which would assist in determining which variable in the above-mentioned set of opportunities for inaccuracy has developed, or if the measured sample of fluid is indeed a true outlier. It is to this end that the present invention has been developed with a view to providing a method for operating a near infrared spectrometer to analyze certain properties of fluids such as properties of motor gasoline and diesel fuels, for example.

SUMMARY OF THE INVENTION

The present invention provides an improved method for operating a near infrared spectrometer to analyze certain properties of fluids such as refined hydrocarbons, including motor gasoline and diesel fuel.

In accordance with an important aspect of the present invention, a method is provided for operating a spectrophotometer of a type which operates in the near infrared region for analyzing certain properties of fluids, including hydrocarbon fluids such as motor gasoline and diesel fuel wherein the analyzer system is diagnosed to verify operating conditions of the analyzer, determine whether or not a reference fluid measurement should be made by the analyzer, or determine whether or not a true outlier condition exists with a measured sample of the fluid being analyzed. The method includes the steps of storing certain data to determine trends in certain operating conditions of the system and the method also includes the step of generation of a fault alarm to indicate when an out-of-specification operating condition exists within the system.

In accordance with another important aspect of the present invention, a fluid property analysis system is operated to measure certain properties of a fluid such as motor gasoline to determine when a prescribed property of the fluid is a true outlier or out-of-specification condition. The method includes capturing a sample of the outlier fluid so that confirmation of the fluid property which is out of specification may be obtained.

Those skilled in the art will appreciate the above-mentioned advantages and superior features of the method of the invention as well as other important aspects thereof upon reading the detailed description which follows in conjunction with the drawing.

DESCRIPTION OF THE PREFERRED EMBODIMENTS

Figure 1:
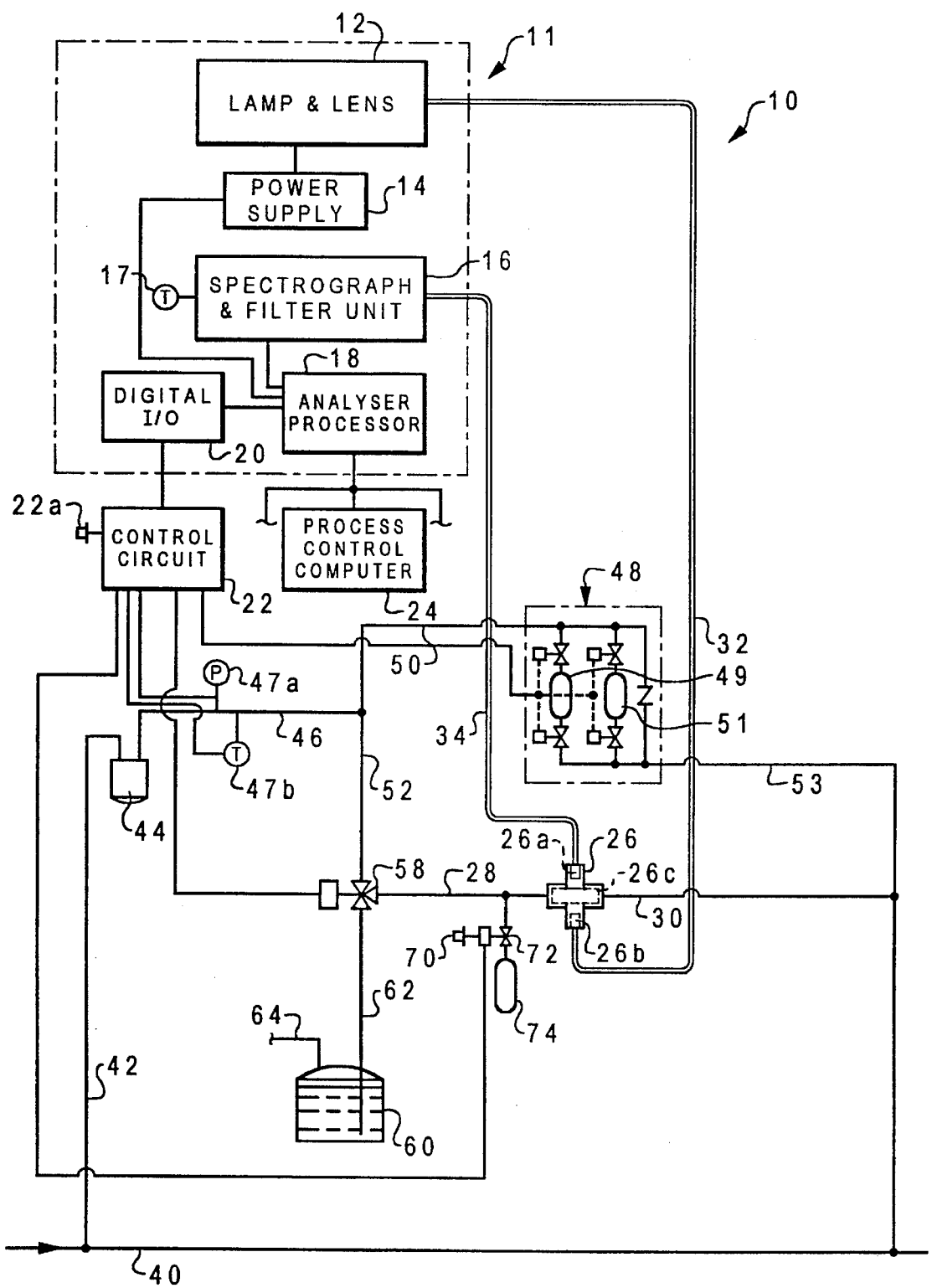
FIG. 1 is a schematic diagram of a system for measuring certain properties of fluid, such as motor gasoline, in accordance with the method of the present invention.

In the description which follows, the reference numerals indicated in the specification correspond to the elements with the same reference numerals set forth in the drawing figures. FIGS. 2 through 9 of the drawing are flow diagrams of certain ones of the steps of the method, which steps may be adapted to be carried out by an electronic digital signal processor operating on appropriate programs.

U.S. Pat. No. 4,963,745 to S. M. Maggard, issued Oct. 16, 1990, describes a process for determining the octane number or other measure of knock avoidance of a hydrocarbon fuel such as motor gasoline or diesel fuel by measuring the near infrared absorbance of certain components of the fuel with sufficient correlation to be used for blending the fuel, for example. FIG. 1 of the drawing illustrates an exemplary system which may be operated in accordance with the method of the present invention to carry out measurements similar to those described in the '745 patent.

Referring to FIG. 1, there is illustrated in schematic form, a diagram of an analyzer system 10 including a near infrared spectrometer, generally designated by the numeral 11, which is characterized by major components shown in block diagram form including a lamp and lens assembly 12, a power supply for the lamp 14, a spectrograph and wavelength filter unit 16, a control processor or "analyzer" processor 18, and an input-output device 20 for converting certain control signals for communication between a control circuit 22 and the processor 18. The processor 18 may be adapted to communicate certain information with one or more process control computers (PCC), one shown and indicated by the numeral 24. The system 10 also includes an element 26 commonly known as a sample probe which is characterized by a housing forming a suitable chamber through which a fluid sample or slipstream may be conveyed by way of conduits 28 and 30. Within the probe 26, electromagnetic radiation in the near infrared portion of the spectrum is communicated across a defined space or chamber 26c occupied by the fluid being analyzed through transmission lines comprising optical fiber cables 32 and 34. The cables 32 and 34 terminate in optical elements or windows 26b and 26a, respectively, which transmit radiation through the chamber

26c. Radiation in the preferred portion of the spectrum is generated by the lamp and lens assembly 12 and communicated through the transmission line 32, the probe 26 and returned to the spectrograph unit 16 by way of the transmission line 34.

A sample slipstream of fluid to be analyzed is conducted to the conduits 28 and 30 from a process flowstream flowing through a conduit 40, for example. Fluid is drawn off from the conduit 40 by way of a suitable conduit 42 and is filtered by a suitable filter unit 44, then communicated through a conduit 46 which is in communication with a fluid sample capture unit 48 and with the probe 26 by way of respective conduits 50 and 52. The conduit 50 is adapted to communicate fluid to one or more fluid sample capture vessels or "bombs" 49 and 51 disposed in the unit 48. Suitable sets of remotely controlled valves are interposed between the conduit 50 and a return conduit 53 for capturing a sample of fluid in either one or both of the vessels 49 and 51. Such valves may be controlled by the processor 18 by way of the circuits 20 and 22.

The probe 26 is placed in fluid flow communication with the sample slipstream by way of the conduit 28 and the return conduit 30 which, together with the conduit 53, is operable to return the sampled fluid to the process flow conduit 40. A motor operated valve 58 is interposed between the conduits 52 and 28 and is adapted to be controlled by the processor 18 through the circuits 20 and 22 for selectively conducting fluid through the probe 26, including the chamber 26c, from the process conduit 40 or from a reference fluid source 60. The source 60 may contain a suitable reference fluid for use in validating the operating condition of the system 10. Toluene, for example, may comprise a suitable reference fluid for use in accordance with the method of the present invention. The source 60 may be maintained at a suitable pressure for causing the reference fluid to flow through a conduit 62, in communication with the valve 58, to the conduit 28 and the probe 26. The amount of reference fluid injected into the circuit comprising the conduits 28, 30 and 40 is not of a sufficient volume to alter the useful properties of the process fluid, such as motor gasoline. The reference fluid is normally caused to flow through the conduit 62 and 28 by a source of pressure gas connected to a supply conduit 64, as illustrated.

Accordingly, the valve 58 may be operated at will to allow the process fluid from the conduit 52 to flow through the probe 26 or, alternatively, to allow the reference fluid to flow from the source 60 through the conduit 28 and the probe 26. The set of control valves illustrated and associated with the sample capture vessel 49 and 51 are controlled to be selectively in open and closed positions to allow part of the fluid flowing through the conduits 42 and 46 to flow through these vessels while the fluid is also flowing through the probe 26. Accordingly, when an outlier condition exists, the capture vessels 49 and/or 51 may be caused to trap a sample of the fluid being analyzed by closing the appropriate valves illustrated on each side of the vessels to capture samples of fluid. The conduit 50 also bypasses the vessels 49 and 51 through a minimum pressure valve in communication with conduit 53.

The components of the system 10 illustrated may include conventional, commercially available, elements. The spectrometer 11, for example, may be of a type manufactured by the Perkin Elmer Corporation of Pomona, Calif. and comprise a model PIONIR 1024 near infrared process analyzer. This analyzer has a spectral range of from 800 to 1100 nm and may measure up to 32 properties of a particular composition being subjected to analysis through the probe 26.

The probe 26 may be of a type also available with the PIONIR 1024 analyzer or of a type described in U.S. patent application Ser. No. 08/120,263, filed Sep. 13, 1993, to Timothy M. Davidson, et al and assigned to the assignee of the present invention.

The system 10 is preferably operated in accordance with an improved method of the present invention which is illustrated generally by the diagrams of FIGS. 2 through 9. Those skilled in the art will recognize that some of the steps of the method may be encoded into a suitable computer program for operating the analyzer processor 18 or a similar central processing unit. The processor 18 may be provided with data in a format whereby measured values of absorbance at predetermined wavelengths of radiation in the near infrared range may be compared with previously prepared data which correlates the desired parameter, for example, octane number of motor gasoline with a particular value of absorbance at a particular wavelength or wavelengths. Moreover, certain operating conditions of the system 10 may also be prescribed such as temperature of the spectrograph and filter unit 16 as indicated by a temperature sensor 17 and fluid pressure and temperature in the sample fluid conduit circuit as measured by sensors 47a and 47b in communication with the conduit 46. Certain other conditions such as the position of the valve 58 and the positions of the valves associated with the sample capture vessels 49 and 51 may also be suitably monitored and committed to a suitable signal storage portion of the processor 18.

The system 10, as commercially available from the source mentioned above, is capable of being provided with data indicating different values of selected parameters for certain compositions including petroleum fuels. The system 10 is operable to store data which correlates a property such as octane number (both research octane number and motor octane number) for compositions such as motor gasoline. Other properties of fuels, which may be correlated with the absorbance of radiation at predetermined wavelengths in the near infrared range, include boiling point, vapor pressure, specific gravity, aromatic content, benzene content, paraffin content, naphthene content, and the content of certain fuel additives such as oxygenates including MTBE, ethanol and methanol, for example. The stored data may then be correlated with a measured radiation absorbance value at a predetermined wavelength or plurality of wavelengths to ascertain whether or not the fluid sample measured by the system 10 is within a suitable range of tolerances. Actual values of the measured parameter may also be recorded for trending. In like manner, values for certain operating conditions of the system 10 such as the power requirement of the lamp and lens system 12 may be continuously or periodically monitored and recorded for trending to determine if the system is operating within a permitted tolerance range or is trending toward an out of tolerance operating condition.

Figure 2:
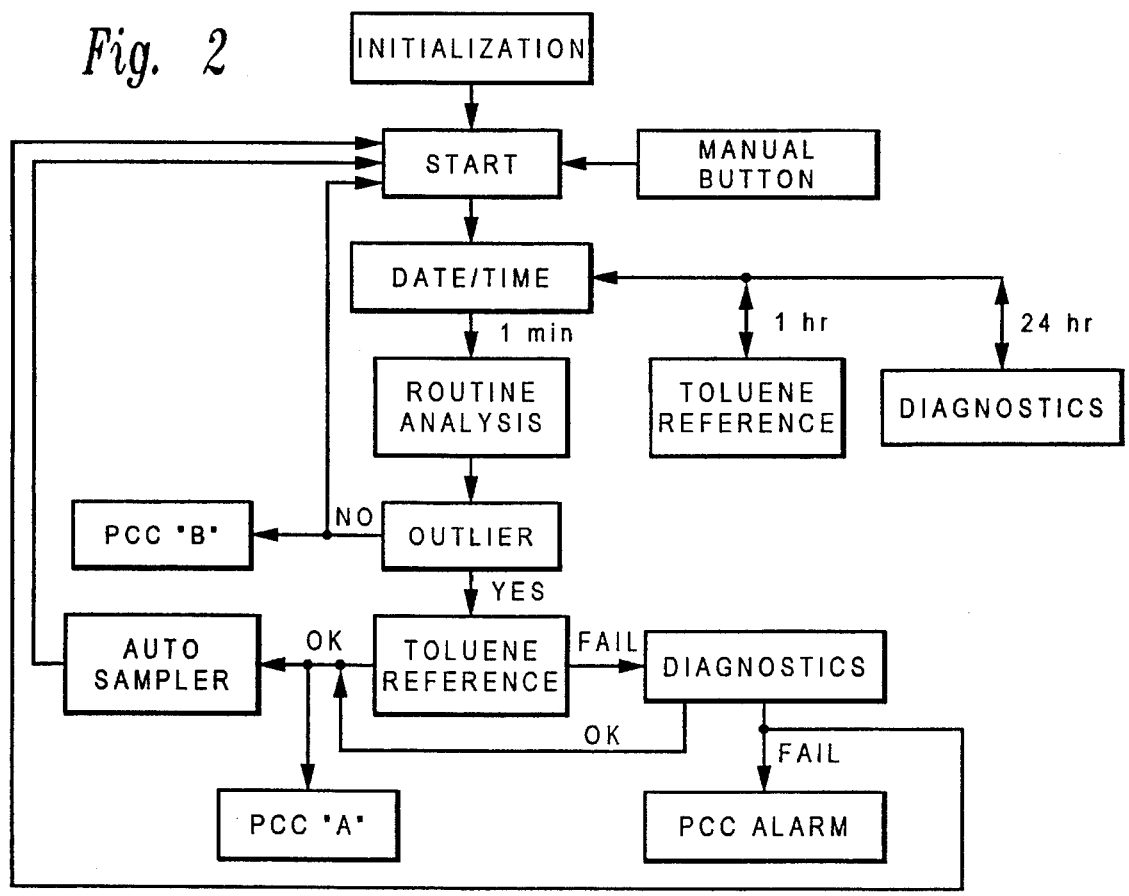
FIGS. 2 through 9 comprise diagrams illustrating certain steps in the method of the present invention.

Referring now to FIGS. 2 through 9, preferred steps in the method of the present invention will now be described in conjunction with the diagrams of the drawing figures. Referring primarily to FIG. 2, there is illustrated the major steps in a preferred method of operating the system 10. The method is initiated with an initialization step which includes several substeps which will be described in further detail herein. If the subroutine of the initialization step indicates that the process may continue, date and time are recorded at preferred intervals, such as one minute indicated in FIG. 2. After recording date and time, a routine sample analysis process may be carried out or, periodically, the operation of the system 10 may be verified by passing a sample of the reference fluid from the source 60 through the probe 26 and comparing the absorbance of radiation by the reference fluid passing with prerecorded data regarding certain properties of the reference fluid. For example, the energy absorbance at predetermined radiation wavelengths for toluene may be compared with predetermined absorbance values to validate whether or not the system 10 is operating normally. As indicated in FIG. 2, the toluene reference subroutine may be carried out periodically such as at one-hour intervals. In like manner, verification of certain operating parameters of the system 10 may be carried out with a so-called diagnostics subroutine which will be explained in further detail herein. In the steps of the diagnostic subroutine, certain operating conditions of the system 10 may be measured and compared to data which has been prerecorded indicating limits on operating conditions of, for example, the power input to the lamp and lens unit 12 and operation of the shutter of the spectrograph and filter unit. The operating condition of the probe 26 may be verified by passing a sample of the reference fluid through the probe.

Referring further to FIG. 2, upon recording date and time, a routine analysis of a fluid sample is carried out at frequent intervals. The aforementioned stored data may be for compositions for certain fuels such as 87 octane, lead-free motor gasoline, and the measured radiation absorbance values of the fluid sample may be compared to the stored data. If the values of absorbance at certain wavelengths which predict octane number, for example, are within a predetermined range of values, then the predicted value of octane number is acceptable and another routine analysis step may be conducted. The recorded value of the routine analysis step may also be transmitted to one or more process control computers such as indicated at PCC "B" in FIG. 2. If the measured values of absorbance for the fluid sample are out of the range of the predicted stored data or model, the operating condition of the system 10 is then verified by performing analysis on a sample of the reference fluid indicated by the major step "toluene reference". If the system 10 is indicated to be operating within predetermined parameters, then the sample capture system 48 or "auto sampler" is operated to capture a sample of the fluid from the conduit 40 through the circuit illustrated in FIG. 1 so that further analysis of the fluid by other methods may be carried out. At the same time, if the sample capture system 48 is activated, indicating that an out of tolerance condition of the fluid being monitored is indicated, another process control computer indicated as PCC "A" may be signaled. Once the "auto sampler" or sample capture system 48 is activated to fill at least one of the vessels 49 or 51 with a fluid sample, the routine analysis method may be started again, as indicated in the diagram of FIG. 2. If another "outlier" condition is observed for the fluid being monitored which exhibits characteristics different from the previous measured outlier condition, the second capture vessel 51 is operated to capture a sample of the fluid being monitored from the conduit 40. The operation of the sample capture system 48 may be operated as often as the number of sample capture vessels available.

If the system 10 indicates that an out of tolerance measurement is obtained for a reference fluid such as toluene, in other words, the system fails the toluene reference test, then the method of the diagnostics subroutine is performed to determine what operating parameter of the system may or may not be within prescribed specifications. If the system fails the diagnostics subroutine, an alarm signal is initiated. This may also be communicated to the process control computer 24 plus any other process control computers which are monitoring operation of the system 10. If the diagnostics subroutine indicates that there is a fault condition in the system 10, a suitable alarm signal is provided to one or more of the process control computers. The routine illustrated in the diagram of FIG. 2 may be repeated, as indicated by the flow line from the diagnostics subroutine step.

Figure 4:
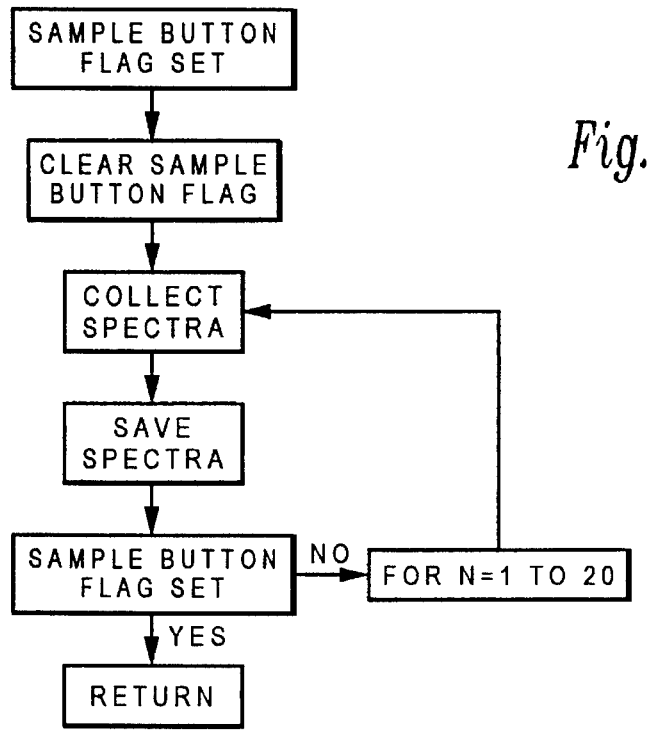

FIGS. 2 and 4 illustrate a part of the method of the present invention wherein a sample of the process fluid being monitored by the system 10 may be captured for analysis and compared with the analysis provided by the system 10. As shown in the diagram of FIG. 1, when a sample button type switch 70 is actuated, a valve 72 opens to provide a sample of the process fluid to a suitable container 74. Actuation of the sample switch 70 may also initiate the steps of FIG. 4 wherein, if the method is being carried out automatically, a reference "flag" is set to indicate that a sample is being collected in the container 74 and that the routine analysis steps are to be carried out to collect data (spectral data of the radiation absorbance at predetermined wavelengths or wave numbers) which is recorded and saved. After the spectra is collected for the sample in question, the process may be repeated if the button type switch 70 is actuated again. If not, the spectra may be collected for the process fluid passing through the probe 26 for a set number of cycles, for example, from 1 to 20 collection and save cycles of spectral data.

Figure 3:
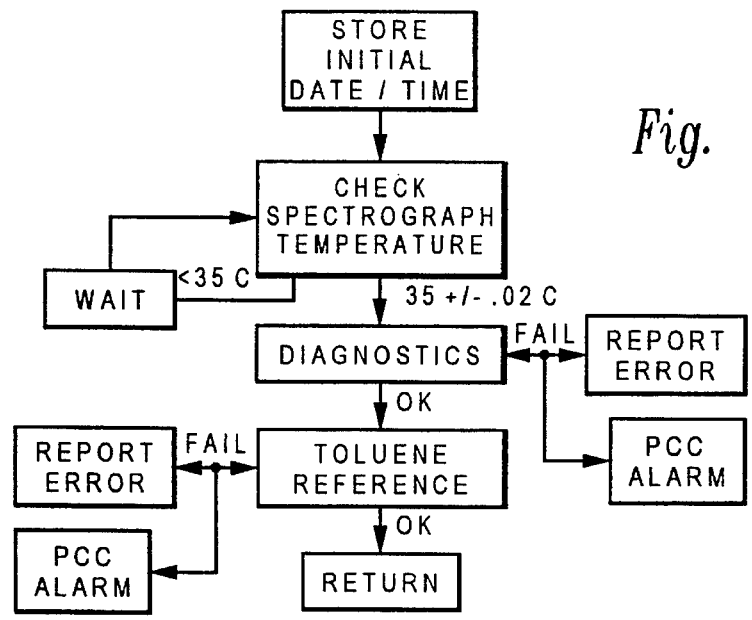

Referring now to FIG. 3, the initialization subroutine is illustrated. Upon initialization of the main operating steps of the method, the initial date and time are stored for future reference and spectrograph temperature is measured. If the spectrograph temperature is not at a predetermined value, such as 35±0.20° C., as indicated in FIG. 3, the next step is to wait until the temperature is to the prescribed value. At this time the diagnostics subroutine may be carried out and if the system 10 fails the steps of the diagnostics test, a suitable alarm is sent to one of the process control computers or otherwise reported. If the diagnostics test is acceptable, then a reference fluid analysis is carried out. If the reference fluid analysis is within the previously recorded predicted range of data, the preferred method is to continue with the method described above and outlined in conjunction with FIG. 2. If the reference fluid analysis is outside the range of previously recorded data, an alarm signal is sent to one of the process control computers or otherwise reported.

Figure 5:
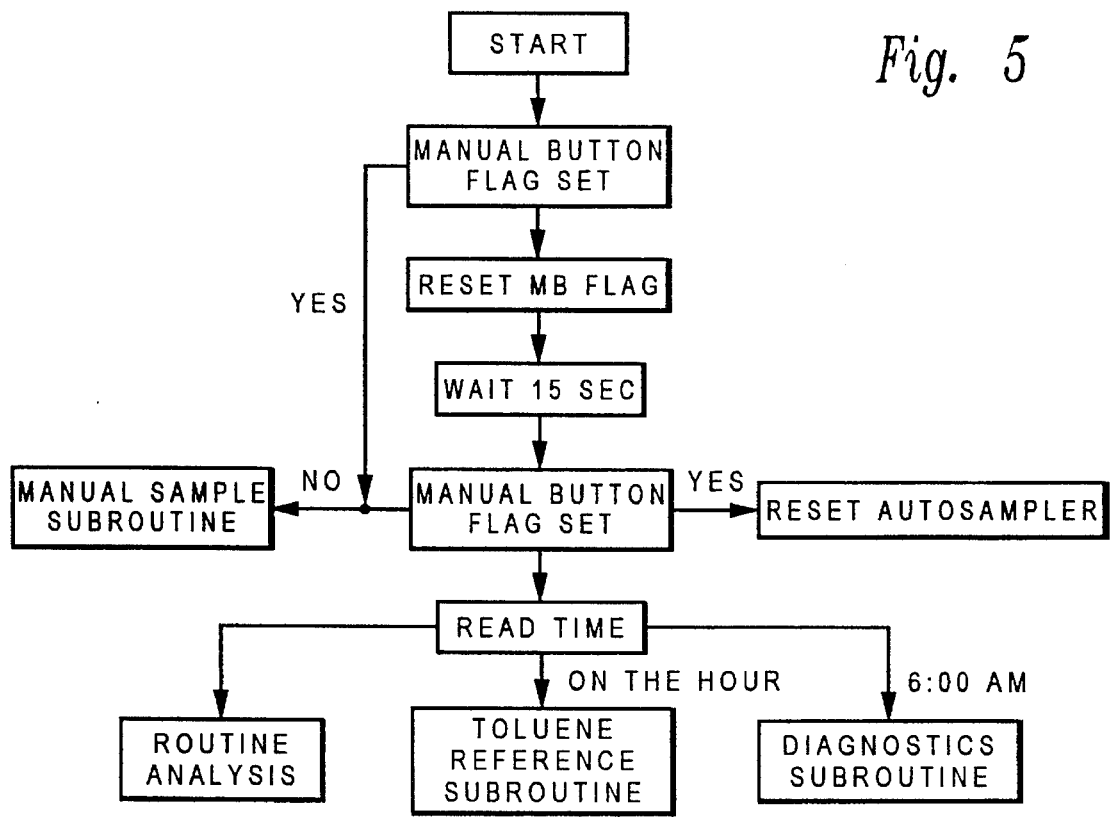

FIG. 5 illustrates the steps in a routine of the method of the invention wherein a sequence of events, which may be automatically programmed, is initiated upon actuation of a manual switch associated with the control circuit 22 and generally designated by the numeral 22a in FIG. 1. If the so-called manual button switch 22a has been actuated at any time in the operation of the system 10, a suitable indicator signal may be initiated at the control circuit 22 and, if this switch 22a is not initiated within a certain predetermined period of time, fifteen (15) seconds for example, the system waits for the routine described above in conjunction with FIG. 4 to be carried out. On the other hand, if the switch 22a is actuated twice within a fifteen (15) second period, or some other predetermined time period, the sample capture system 48 may be automatically reset so that the valves to one of the capture vessels 49 are open while the valves to the other sample capture vessel or vessels are closed, for example. When the sample capture system 48 is ready, the method of the invention may then proceed to read the time and conduct either the routine analysis steps of the method to be described hereinbelow, perform the reference fluid validation steps described in conjunction with FIG. 6, or perform the steps of the diagnostics subroutine described in conjunction with FIG. 7 at a predetermined time.

Figure 6:
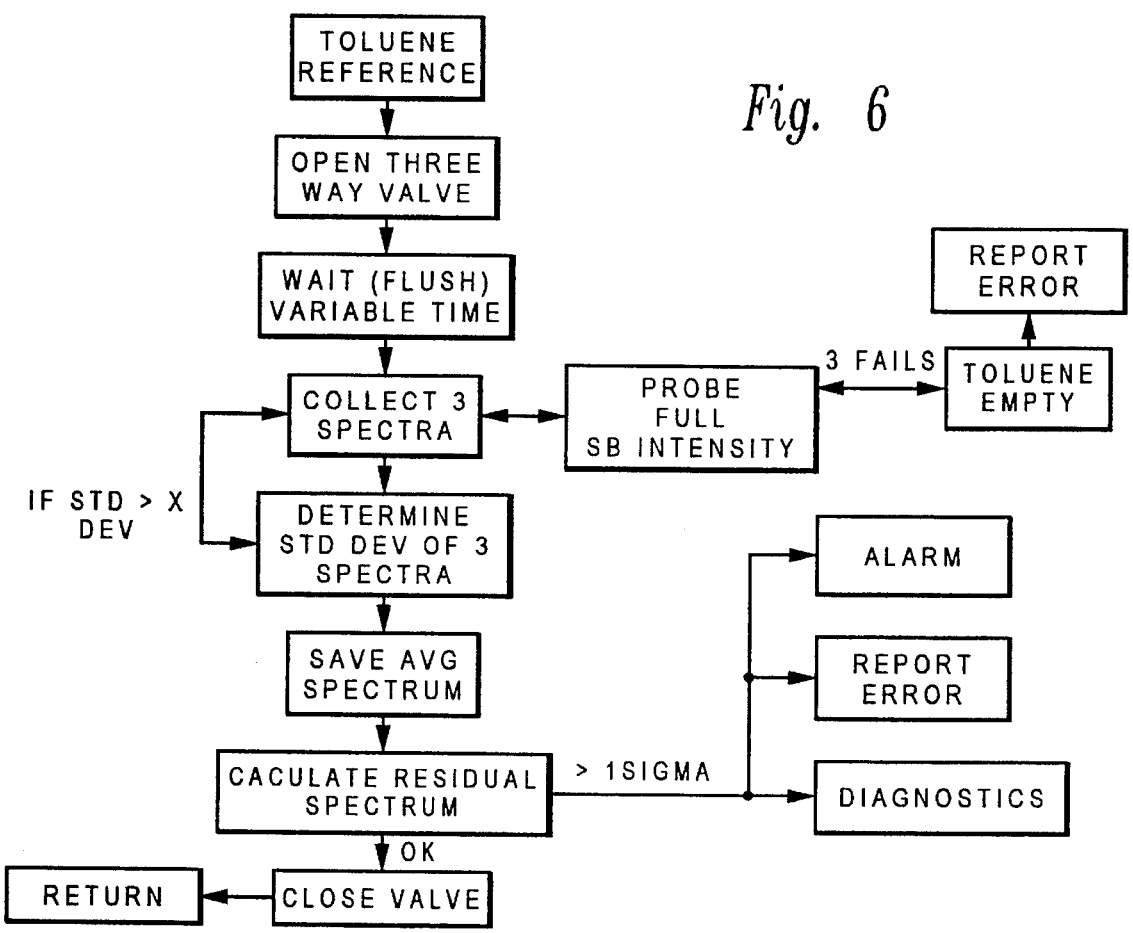

Referring now to FIG. 6, there is illustrated a flow diagram of the steps for operating the system 10 with a reference fluid such as toluene. When the system 10 is operated to analyze the absorbance characteristics of a sample of reference fluid, the valve 58, FIG. 1, is operated to place the source 60 in communication with the probe 26 so that reference fluid may be allowed to flow through the probe. In order to assure that a sample of reference fluid is the only fluid occupying the probe, a predetermined time delay is initiated upon opening the valve 58 to flush the conduits 28 and 30 and the sample chamber of the probe 26. After a predetermined time, at least three separate measurements are made of the absorbance of radiation by a sample of the reference fluid. A standard deviation is calculated to determine if the system 10 is operating in a stable manner. If the standard deviation of the predetermined number of absorbance measurements is greater than a specified limit, another predetermined number of absorbance measurements over a predetermined spectrum may be made and the data recorded. This routine may be repeated a predetermined number of times, say for a total of three sets of three spectra and, if it is indicated that the system 10 is not operating in a stable manner, an alarm signal will be initiated. If the measured intensity of the radiation signal exceeds a predetermined amount outside the normal range of intensity variation expected with fluid in the probe 26 and after a plurality of verifications of an out of range intensity level signal, an alarm may be sounded to indicate that the reference fluid source is empty or at least the probe examination chamber is not full of reference fluid. After the system 10 has been indicated to be operated in a stable mode, a residual spectrum is determined and, if the residual spectrum values are greater than a predetermined threshold value, an alarm signal is reported and the steps of the diagnostics routine are carried out. If the residual spectrum values are within predetermined limits, the valve 58 is again placed in communication with the fluid whose properties are being routinely analyzed and the operating system is caused to carry out the steps of the routine analysis.

Figure 7:
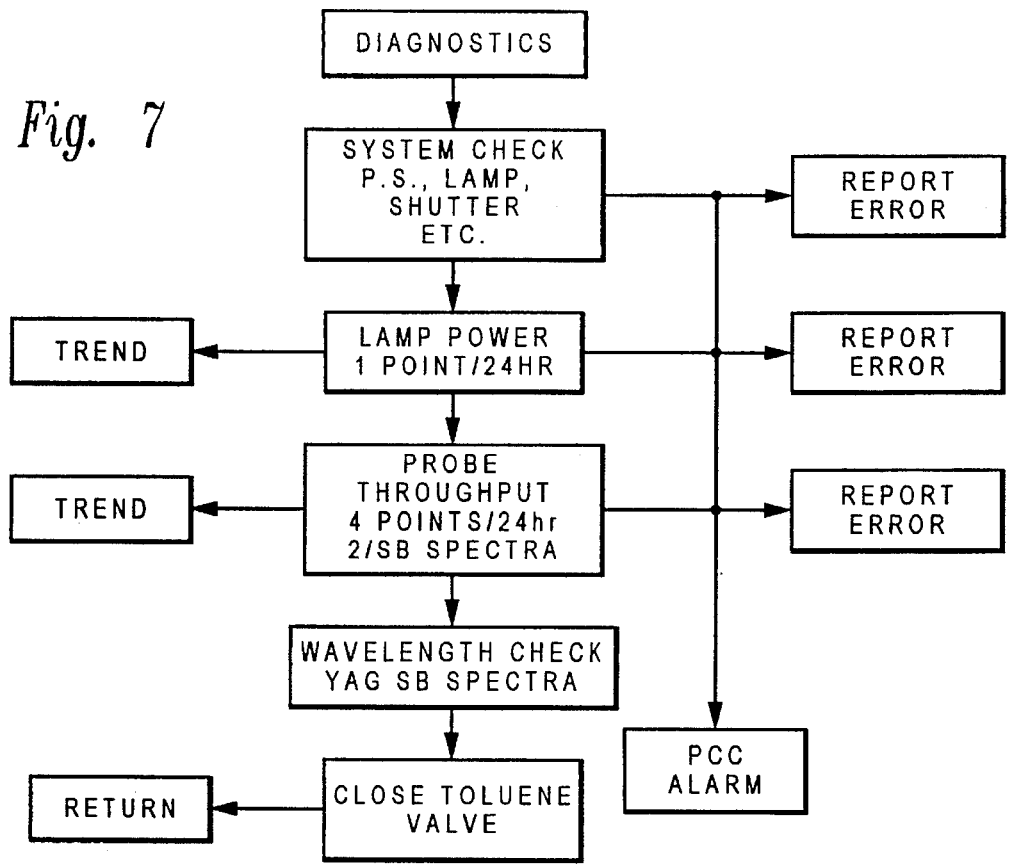

Referring now to FIG. 7, there is illustrated a flow diagram of the major steps of the so-called diagnostics routine wherein certain operating conditions of the system 10 are monitored on a periodic basis. If the operating conditions of the system 10 are outside a predetermined tolerance range for any of the parameters being monitored, then an alarm signal is sent to one of the process control computers and the particular parameter which is out of tolerance is reported. An important parameter to be monitored in operating a near infrared spectrometer is power input to the radiation generating "lamp". In this regard, it may be desirable to record power input to the lamp on a periodic basis and record the values of power to establish a trend to indicate when the lamp should be replaced before total failure.

In like manner, during the diagnostic routine, a change in radiation absorbance of the reference fluid at particular wavelengths such as 820 nm and 1050 nm (for toluene) may be obtained to determine foreground and background spectrum values. These values are preferably saved and recorded to establish a trend in any changes in absorbance to determine whether or not the probe requires cleaning of the optical fiber window surfaces. A wavelength verification value is also recorded by collecting a reference spectrum such as a neodenium-yag spectrum. If any of these values are out of tolerance, then a signal is also sent to the process control computer as an alarm signal and the error signal is recorded and suitably displayed by the system 10. After the diagnostics routine is finished, the valve 58 is then, of course, moved to a position to allow the process fluid being analyzed to again flow through the probe 26.

Figure 8:
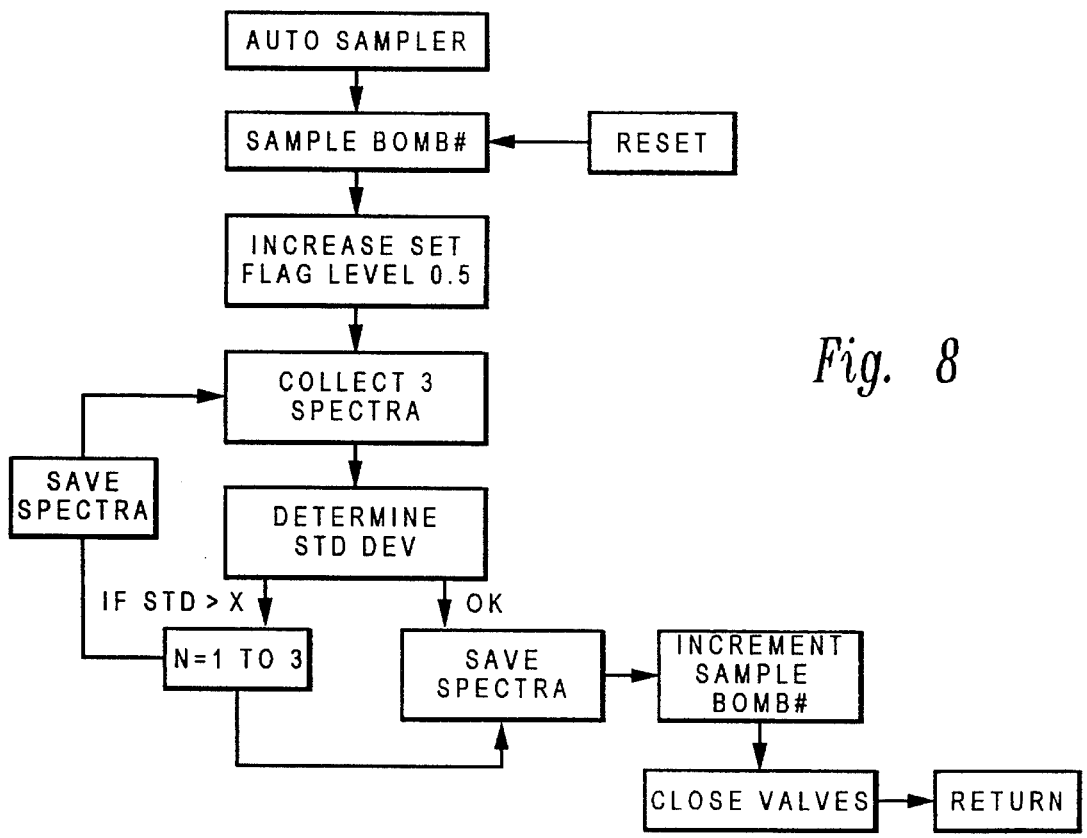

Referring to FIG. 8, the steps carried out in operating the sample capture system 48 or auto sampler are indicated by the flow diagram. Once operation of the sample capture system 48 is initiated to capture a sample in one of the vessels 49 or 51, the threshold of out of range radiation absorbance valves which will initiate capturing a sample in the next vessel is raised a predetermined amount and, simultaneously, the system 10 is operated to record three measurements of the spectra of the fluid being processed through the probe 26. A suitable statistical calculation such as a standard deviation calculation is then carried out on the measured spectra. If the deviation is above acceptable limits, then the measurement is repeated a predetermined number of times and the valves to a particular capture vessel are closed and the valves permitting flow to the next capture vessel are opened so that a sample of the out of specification fluid is saved in one of the capture vessels. The method steps may then include return to the main fluid analysis routine of the system 10.

Figure 9:
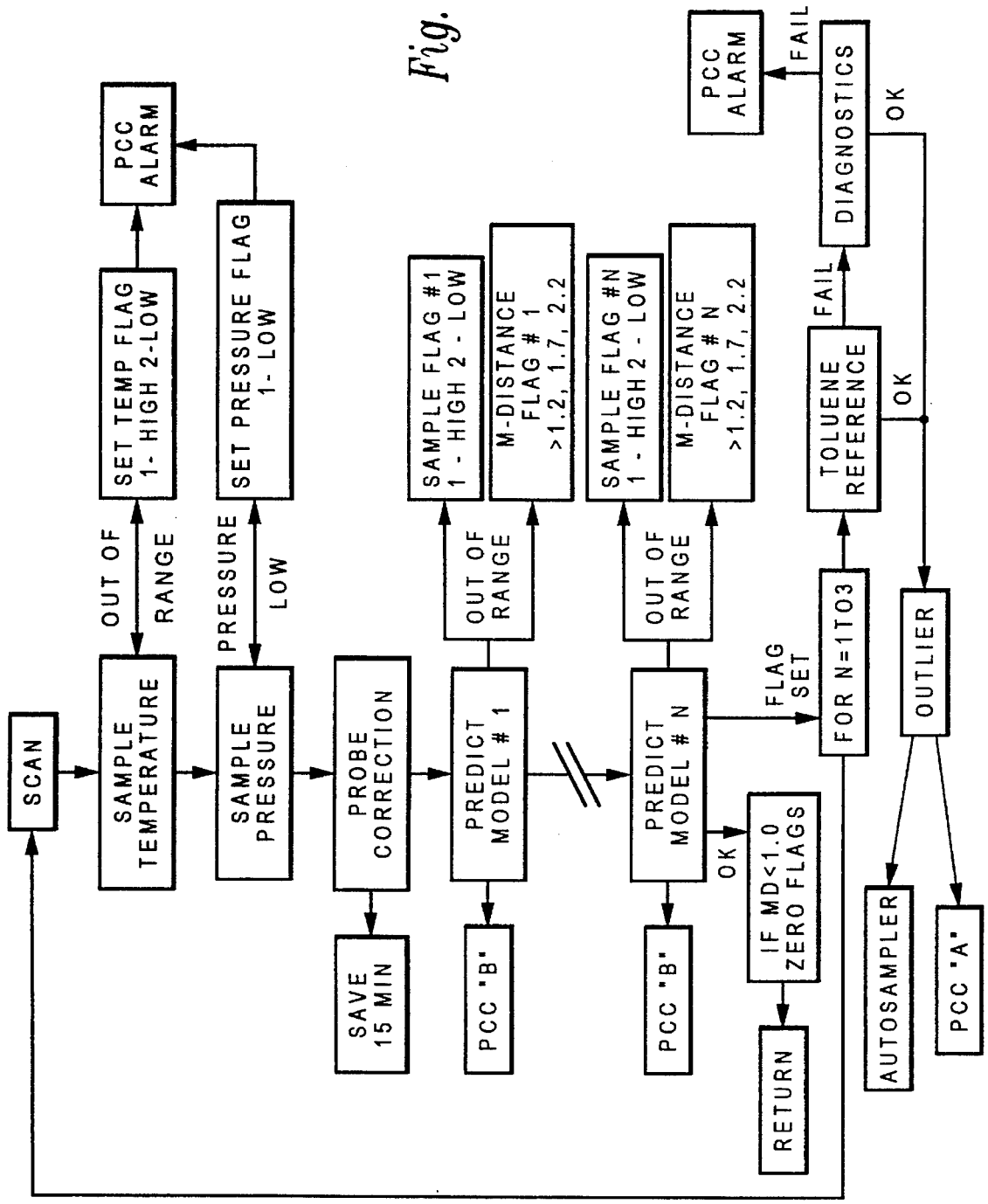

Referring now to FIG. 9, there is illustrated a diagram of the so-called routine fluid analysis method of the present invention using a system such as the system 10. As indicated in FIG. 2, if the particular fluid being analyzed is known, then the training set or model of radiation values against which the samples analyzed are compared, will be brought into view so that the sample values measured may be compared with the model or training set values. In the routine analysis method, the temperature and pressure of the fluid being analyzed are recorded as sensed by the sensors 47a and 47b. If the sample fluid temperature or pressure are out of range, then this condition is recorded and an alarm signal is sent to one of the process control computers. The next step would be to verify the operating condition of the sample probe 26 to determine if the optical elements 26a and 26b, FIG. 1, are subject to any error inducing conditions such as the formation of a film on the surfaces of the elements. Depending on the type of analyzer being used, there may be built in correction factors for correcting the variations in the probe transmissivity. After probe correction is carried out, a routine analysis of a sample begins by comparing the spectra of the desired property of a sample with the stored data for that property which will enable the prediction of the property. If the measured values are within a suitable range, the value is transmitted to one of the process control computers. If the measured value is out of range, a signal indicating either a "high" or "low" condition is given and the Mahalanobis Distance (M-DISTANCE) and/or residual ratio of the measured values is calculated. If the Mahalanobis Distance is greater than a predetermined value, another signal is indicated. If more than one property is being measured, then the spectra collected for a sample is compared with the model for that property, as indicated by the flow diagram.

If all of the properties being measured are within range and there are no signal "flags", as indicated, the steps of the operating method are continuously repeated or, as indicated in the diagram, the steps of the method are repeated. The diagram of FIG. 9 indicates this by the box labeled "Return". If any one of the properties compared with the model or models for that property is out of range, then the property is measured two more times. If, after three "flags" or out of range signals are indicated, the reference fluid (toluene) analysis method is initiated. If the reference fluid analysis indicates that the operating condition of the system is within limits, then an "outlier" condition is indicated and the "auto sampler" or sample capture steps of the method are initiated to capture a sample of the out of specification fluid. A signal is also sent to one of the process control computers indicating that a sample is being captured which is out of specification.

Alternatively, if the reference fluid steps indicate an out of range condition, then the system 10 is subjected to the steps of the "diagnostics" routine previously described. If the system fails the steps of the diagnostics routine, then an alarm signal is sent to one or more of the process control computers. On the other hand, if the system operating conditions are indicated to be acceptable pursuant to the diagnostics routine method, then an outlier condition is also declared, as indicated by the diagram of FIG. 9.

A computer operating program may be developed to carry out the method of the invention as set forth above and illustrated in the diagrams of FIGS. 2 through 9. For example, on start-up of the system 10, date and time would be recorded. The temperature of the spectrograph 11 is checked and the system 10 would wait for this temperature to stabilize within predetermined limits. Once the temperature is stable, then the steps of the diagnostic method would be initiated and selected parameters measured during these steps might be recorded to determine whether an adverse trend was developing. Of course, if the diagnostics routine indicates a condition which is out of specification for the system 10, then an alarm signal is initiated and the error is recorded.

After the diagnostics routine is completed a reference fluid routine, in accordance with the method of the invention, is carried out as described above. Once the reference fluid operating routine is completed and is within specification, the next step would be to verify whether or not the manual sample routine has been initiated or not. If the manual sample routine has been initiated or indicated to have been initiated, a predetermined time is allowed to lapse to allow an operator to initiate the manual sample routine again if the manual sample routine is initiated a second time, then the sample capture or auto sampler routine is carried out. Otherwise, the system 10 then begins the routine analysis steps described above.

Each time the routine analysis method is initiated, the time is noted and if the time is at a predetermined hour, then the toluene reference routine or the diagnostics routine are run in accordance with their predetermined initiation times.

The regular sample analysis steps are carried out and the values of the various properties being analyzed are routinely sent out to the process control computers. If a property value is out of range, then the steps of the routine analysis are repeated to collect a total of three sets of values and if the average of the three sets is out of range, the reference fluid and diagnostics routines are initiated to verify the operating condition of the system. If the system is indicated to be operating within specification, then the plural samples of spectral data are collected and recorded and, if the deviation is out of range after the predetermined number of measurements, a sample capture vessel is isolated by closing the appropriate valves and a signal is recorded to indicate that another sample capture vessel is placed in condition to capture a sample of the fluid being analyzed. Detection of an outlier is, of course, signaled to the appropriate process control computer, a system display, if provided, or some other indicator which will notify system operating personnel that the fluid being analyzed is out of specification. The system 10 may be operated to continuously reset itself to carry out the steps indicated downstream of the start condition indicated in FIG. 2.

Although a preferred embodiment of a method for operating a fluid analysis system for analyzing certain properties of a fluid by measurement of the absorbance of electromagnetic radiation has been described in detail herein, those skilled in the art will recognize that various substitutions and modifications may be made to the steps of the method without departing from the scope and spirit of the invention as recited in the appended claims.

What is claimed is:

1. A method of operating a system for measuring selected properties of a hydrocarbon fuel by the absorbance of near infrared electromagnetic radiation of predetermined wavelengths of said radiation wherein said system includes a source of said radiation, a spectrograph, a probe through which said hydrocarbon fuel and said radiation are passed, and conduit means for conducting said hydrocarbon fuel to and from said probe, said method comprising the steps of:

measuring at least one operating parameter of said system selected from the group consisting of power input to said source of radiation, the temperature of said spectrograph, and the transmissivity of radiation through said probe and comparing the measurement of said at least one operating parameter with prerecorded limits on said at least one operating parameter and verifying that said at least one operating parameter is within said prerecorded limits.

introducing a reference fluid into said probe and measuring at least one property of said reference fluid by measuring the absorbance of radiation transmitted to said probe and through said reference fluid and comparing the measured absorbance with absorbance values corresponding to said at least one property of said reference fluid;

providing a signal if said at least one property of said reference fluid is not within a predetermined range;

introducing a sample of a hydrocarbon fuel to be analyzed into said probe and measuring the alteration of radiation signals transmitted through said probe to determine a value of a selected property of said hydrocarbon fuel;

repeating at least one of the steps of measuring at least one property of said reference fluid and one of said operating parameters of said system if said value of said selected property of said hydrocarbon fuel is not within a predetermined range of values; and capturing a sample of said hydrocarbon fuel if said steps of measuring the at least one property of said reference fluid and of determining said selected property of said hydrocarbon fuel indicates that the selected property of said hydrocarbon fuel measured is not within a predetermined range of values.

2. The method set forth in claim I including the step of:

repeating the measurement of said selected property of said hydrocarbon fuel a predetermined number of times if the first measurement of said selected property of said hydrocarbon fuel indicates a property value that is not within a predetermined limit.

3. The method set forth in claim 1 including the steps of:

recording the date and time of measurement of said hydrocarbon fuel.

4. The method set forth in claims 1 or 3 including the step of:

measuring a selected property value of said reference fluid based on the absorbance of radiation by said reference fluid periodically at predetermined time intervals.

5. The method set forth in claim 1 wherein:

the step of measuring said at least one operating parameter of said system is carried out at a predetermined time interval.

6. The method set forth in claim 1 including the step of:

measuring the temperature of said spectrograph before carrying out the steps of measuring said property of said reference fluid and measuring said at least one operating parameter of said system; and repeating the step of measuring the temperature of said spectrograph until said temperature reaches a predetermined value before measuring said at least one property of said reference fluid and said at least one operating parameter.

7. The method set forth in claim 1 including the step of:

introducing said reference fluid into said probe and waiting a predetermined period of time before measuring said at least one property of said reference fluid in said probe.

8. The method set forth in claim 7 including the step of:

making plural measurements of said at least one property of said reference fluid and determining the standard deviation of said measurements from a predetermined value of said at least one property of said reference fluid.

9. The method set forth in claim 8 including the step of:

measuring the intensity of a radiation signal passing through said probe to determine if said probe is occupied by said reference fluid.

10. The method set forth in claim 8 including the step of:

measuring the values of said operating parameters of said system if the measured values of said at least one property of said reference fluid is not within a predetermined range of values.

11. The method set forth in claim 1 wherein:

said system includes plural sample capture vessels and said method includes the steps of:

capturing a sample of said hydrocarbon fuel in one of said vessels;

capturing a sample of said hydrocarbon fuel in another of said vessels when a measured property of said hydrocarbon fuel deviates from a predetermined reference value of said property.

12. The method set forth in claim 1 including the step of:

collecting a sample of said hydrocarbon fuel passing through said probe and measuring a property of said hydrocarbon fuel concomitantly with the collection of said sample of said hydrocarbon fuel a predetermined number of times.

13. The method set forth in claim 1 wherein said hydrocarbon fuel is a liquid at test conditions.

14. The method set forth in claim 1 wherein said hydrocarbon fuel is gasoline and said selected property is octane.

15. The method set forth in claim 1 wherein said hydrocarbon fuel is diesel fuel.

\* \* \* \* \*